(12) United States Patent
Wood

(10) Patent No.: US 9,072,479 B2
(45) Date of Patent: Jul. 7, 2015

(54) VARIABLE CONTROL FOR HANDHELD DEVICE

(75) Inventor: Robert J. Wood, Syracuse, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 488 days.

(21) Appl. No.: 13/102,119

(22) Filed: May 6, 2011

(65) Prior Publication Data

US 2012/0280576 A1    Nov. 8, 2012

(51) Int. Cl.
  *A61B 1/267*  (2006.01)
  *A61B 1/227*  (2006.01)
  *H03K 17/96*  (2006.01)

(52) U.S. Cl.
  CPC ............. *A61B 1/227* (2013.01); *Y10T 307/826* (2015.04); *H03K 17/962* (2013.01); *H03K 2217/96066* (2013.01)

(58) Field of Classification Search
  CPC ...................................... A61B 1/227
  USPC ........ 600/180, 200; 345/173–184; 178/18.06; 323/222
  See application file for complete search history.

(56) References Cited

U.S. PATENT DOCUMENTS

| | | | |
|---|---|---|---|
| 4,442,382 A | | 4/1984 | Fleck |
| 4,532,918 A * | | 8/1985 | Wheeler .................... 600/109 |
| 4,609,861 A | | 9/1986 | Inaniwa et al. |
| 4,643,171 A * | | 2/1987 | Riester ...................... 600/200 |
| 5,653,238 A * | | 8/1997 | Pompei ...................... 600/474 |
| 5,717,311 A | | 2/1998 | Im et al. |
| 6,094,033 A | | 7/2000 | Ding et al. |
| 6,219,573 B1 * | | 4/2001 | Pompei ...................... 600/474 |
| 6,300,728 B1 * | | 10/2001 | Blackburn et al. ........... 315/307 |
| 6,319,199 B1 * | | 11/2001 | Sheehan et al. ............. 600/200 |
| 6,320,354 B1 * | | 11/2001 | Sengupta et al. ........... 320/132 |
| 6,329,727 B1 * | | 12/2001 | Traveis et al. ............... 307/115 |
| 6,447,448 B1 * | | 9/2002 | Ishikawa et al. ............ 600/300 |
| 6,459,175 B1 * | | 10/2002 | Potega ...................... 307/149 |
| 6,700,352 B1 | | 3/2004 | Elliott et al. |
| 6,788,151 B2 * | | 9/2004 | Shvarts et al. .............. 330/297 |
| 7,002,265 B2 * | | 2/2006 | Potega ...................... 307/149 |

(Continued)

FOREIGN PATENT DOCUMENTS

| | | |
|---|---|---|
| EP | 2090256 A2 | 8/2009 |
| JP | 2008-067323 A | 3/2008 |

(Continued)

OTHER PUBLICATIONS

Dirjish; Ultracapacitors Branch Out Into Wider Markets; Electronic Design, © 2010 Penton Media, Inc.; Nov. 17, 2008; accessed May 4, 2011 via: electronicdesign.com/ . . . /ultracapacitor . . . ; 3 pgs.

(Continued)

*Primary Examiner* — Eduardo C Robert
*Assistant Examiner* — Stuart S Bray
(74) *Attorney, Agent, or Firm* — Merchant & Gould P.C.

(57) ABSTRACT

A handheld device includes a capacitance sensing variable control that detects the presence of and movement of a user's finger on an external surface of the device. The handheld device also includes a variable output power supply and an electronic device that is powered by the variable output power supply. Upon detection of the movement on the external surface of the device, the output of the variable output power supply is adjusted. The adjusted output changes the operation of the electronic device.

14 Claims, 11 Drawing Sheets

(56) References Cited

U.S. PATENT DOCUMENTS

| | | | |
|---|---|---|---|
| 7,081,743 B2* | 7/2006 | Liu et al. | 323/317 |
| 7,082,824 B2* | 8/2006 | Lull | 73/204.15 |
| 7,323,849 B1 | 1/2008 | Robinett et al. | |
| 7,327,850 B2* | 2/2008 | Crump et al. | 381/74 |
| 8,027,175 B2* | 9/2011 | Liu et al. | 363/16 |
| 8,330,633 B2* | 12/2012 | Brubaker et al. | 341/136 |
| 8,345,398 B2* | 1/2013 | Mazzarisi et al. | 361/93.9 |
| 8,543,216 B2* | 9/2013 | Carbunaru et al. | 607/61 |
| 8,556,891 B2* | 10/2013 | Mathur | 606/34 |
| 8,579,893 B2* | 11/2013 | Hoey | 606/41 |
| 8,612,159 B2* | 12/2013 | Say et al. | 702/19 |
| 8,917,256 B2* | 12/2014 | Roziere | 345/174 |
| 2001/0015578 A1* | 8/2001 | Westlake | 307/125 |
| 2002/0038076 A1* | 3/2002 | Sheehan et al. | 600/200 |
| 2003/0080712 A1 | 5/2003 | Tamura et al. | |
| 2003/0102845 A1 | 6/2003 | Aker et al. | |
| 2003/0171655 A1* | 9/2003 | Newman et al. | 600/200 |
| 2004/0186352 A1* | 9/2004 | Roberts et al. | 600/200 |
| 2004/0251880 A1 | 12/2004 | O'Brien | |
| 2004/0263129 A1 | 12/2004 | Thrap | |
| 2005/0038388 A1 | 2/2005 | Hommann et al. | |
| 2006/0055679 A1* | 3/2006 | Grinshpoon et al. | 345/173 |
| 2006/0189863 A1* | 8/2006 | Peyser et al. | 600/345 |
| 2007/0132737 A1* | 6/2007 | Mulligan et al. | 345/173 |
| 2007/0229468 A1* | 10/2007 | Peng et al. | 345/173 |
| 2007/0234091 A1* | 10/2007 | Vishin et al. | 713/322 |
| 2008/0018308 A1 | 1/2008 | Daboussi | |
| 2008/0111423 A1 | 5/2008 | Baker et al. | |
| 2008/0129219 A1* | 6/2008 | Smith et al. | 315/291 |
| 2008/0208297 A1* | 8/2008 | Gertner et al. | 607/92 |
| 2008/0258674 A1 | 10/2008 | Hui et al. | |
| 2008/0272656 A1 | 11/2008 | Mason | |
| 2009/0009491 A1* | 1/2009 | Grivna | 345/184 |
| 2009/0015216 A1 | 1/2009 | Seberger et al. | |
| 2009/0096430 A1 | 4/2009 | Van Der Linde et al. | |
| 2009/0179613 A1 | 7/2009 | Masho | |
| 2009/0209990 A1 | 8/2009 | Yates et al. | |
| 2009/0306479 A1* | 12/2009 | Kamihara | 600/180 |
| 2010/0007307 A1 | 1/2010 | Baarman et al. | |
| 2010/0094110 A1* | 4/2010 | Heller et al. | 600/345 |
| 2010/0094111 A1* | 4/2010 | Heller et al. | 600/345 |
| 2010/0094220 A1 | 4/2010 | Mandro | |
| 2010/0137779 A1 | 6/2010 | Seitz | |
| 2010/0157638 A1 | 6/2010 | Naiknaware et al. | |
| 2010/0182075 A1 | 7/2010 | Yang et al. | |
| 2010/0225283 A1 | 9/2010 | Hsia et al. | |
| 2011/0046432 A1* | 2/2011 | Simon et al. | 600/14 |
| 2011/0100728 A1* | 5/2011 | Chen | 178/18.06 |
| 2011/0105910 A1* | 5/2011 | Lawson et al. | 600/474 |
| 2011/0125213 A1* | 5/2011 | Simon et al. | 607/42 |
| 2011/0221417 A1* | 9/2011 | Ishidoh et al. | 323/288 |
| 2011/0316339 A1* | 12/2011 | Trivedi et al. | 307/31 |
| 2012/0004509 A1* | 1/2012 | deLucia | 600/199 |
| 2012/0019467 A1* | 1/2012 | Hotelling et al. | 345/173 |
| 2012/0068952 A1* | 3/2012 | Slaby et al. | 345/173 |
| 2012/0072157 A1* | 3/2012 | Alameh et al. | 702/99 |
| 2012/0146943 A1* | 6/2012 | Fairley et al. | 345/174 |
| 2012/0157776 A1* | 6/2012 | Wood | 600/200 |
| 2012/0169650 A1* | 7/2012 | Chang | 345/174 |
| 2012/0169651 A1* | 7/2012 | Chang | 345/174 |
| 2012/0169652 A1* | 7/2012 | Chang | 345/174 |
| 2012/0169653 A1* | 7/2012 | Chang | 345/174 |
| 2012/0169655 A1* | 7/2012 | Chang | 345/174 |
| 2012/0169656 A1* | 7/2012 | Chang | 345/174 |
| 2012/0313892 A1* | 12/2012 | Philipp | 345/174 |
| 2013/0066168 A1* | 3/2013 | Yang et al. | 600/301 |
| 2013/0177220 A1* | 7/2013 | Erhart et al. | 382/124 |
| 2013/0187704 A1* | 7/2013 | Edwards | 327/517 |
| 2013/0187891 A1* | 7/2013 | Eriksson et al. | 345/175 |

FOREIGN PATENT DOCUMENTS

| | | |
|---|---|---|
| WO | WO 2006/060391 | 6/2006 |
| WO | WO 2008/093170 | 8/2008 |

OTHER PUBLICATIONS

Isaacson et al.; Advanced Lithium Ion Battery Charger; Lockheed-Martin Missiles & Space, P.O. Box 3504, Sunnyvale, CA; 94089-3504; © 2000, pp. 193-198.

Park Chulsung et al.; TurboCap: A Batteryless, Supercapacitor-based Power Supply for Mini-FDPM; The University of California; Irvine, CA 92697-2625 USA and National Tsing Hua, Hsinchu, Taiwan; 8 pgs.

Li et al.; A Wireless Power Interface for Rechargeable Battery Operated Medical Implants; IEEE Transactions on Circuits and Systems II: Express Briefs, vol. 54 Issue 10, Oct. 2007; pp. 912-916.

Simjee et al.; Efficient Charging of Supercapacitors for Extended Lifetime of Wireless Sensor Nodes; IEEE Transactions on Power Electronics, vol. 23 No. 3, May 2008; © 2008 IEEE; pp. 1526-1536.

* cited by examiner

VARIABLE CONTROL FOR HANDHELD DEVICE

BACKGROUND

Healthcare providers, such as doctors and nurses, frequently use handheld devices when providing healthcare. Many of these handheld devices include electrical devices that must be powered by electricity. One example of such a handheld device is an otoscope, which includes a light to illuminate a patient's ear canal during an examination. It is sometimes desirable to adjust the electrical device, such as to increase or decrease the brightness of the light.

SUMMARY

In general terms, this disclosure is directed to a device including a capacitance sensitive control. In one possible configuration and by non-limiting example, the capacitance sensitive control detects an input in the form of a sliding movement across an external surface of a housing. In some embodiments the sliding movement is used to adjust an amount of power delivered by a variable power supply.

One aspect is a device including an instrument, a variable output power supply, and a variable control. The instrument includes an electronic device. The variable output power supply is electrically connected to the electronic device. The variable control detects the capacitance of and movement of a user's finger on an external surface of the device. The variable control comprises at least three spaced conductive strips separated from the exterior surface by an electrically insulating material. The variable output power supply is adjusted upon detection of movement by the variable control.

Another aspect is a method of controlling a device. The method includes: detecting a presence of a finger at an external surface of the device by detecting a change of a capacitance; detecting movement of the finger in a direction along the external surface; and adjusting a variable output power supply based on the detected movement.

Yet another aspect is a medical instrument including an electronic device that performs an operation, wherein the operation is modified by changing a magnitude of power supplied to the electronic device; and a power handle coupled to the medical instrument. The power handle includes a housing, a capacitance sensing variable control, a power source, and a variable power supply. The housing includes an external surface. The capacitance sensing variable control is sealed within the housing and separated from the external surface by an insulating material. The capacitance sensing variable control includes at least three spaced conductive strips arranged and configured to detect a sliding movement of a finger along the external surface. The power source is within the housing. The variable power supply is within the housing and electrically coupled to supply power to the electronic device, wherein the variable power supply receives an input with the capacitive sensor and adjusts the power supplied to the electronic device based on the input.

DETAILED DESCRIPTION

Figure 1:
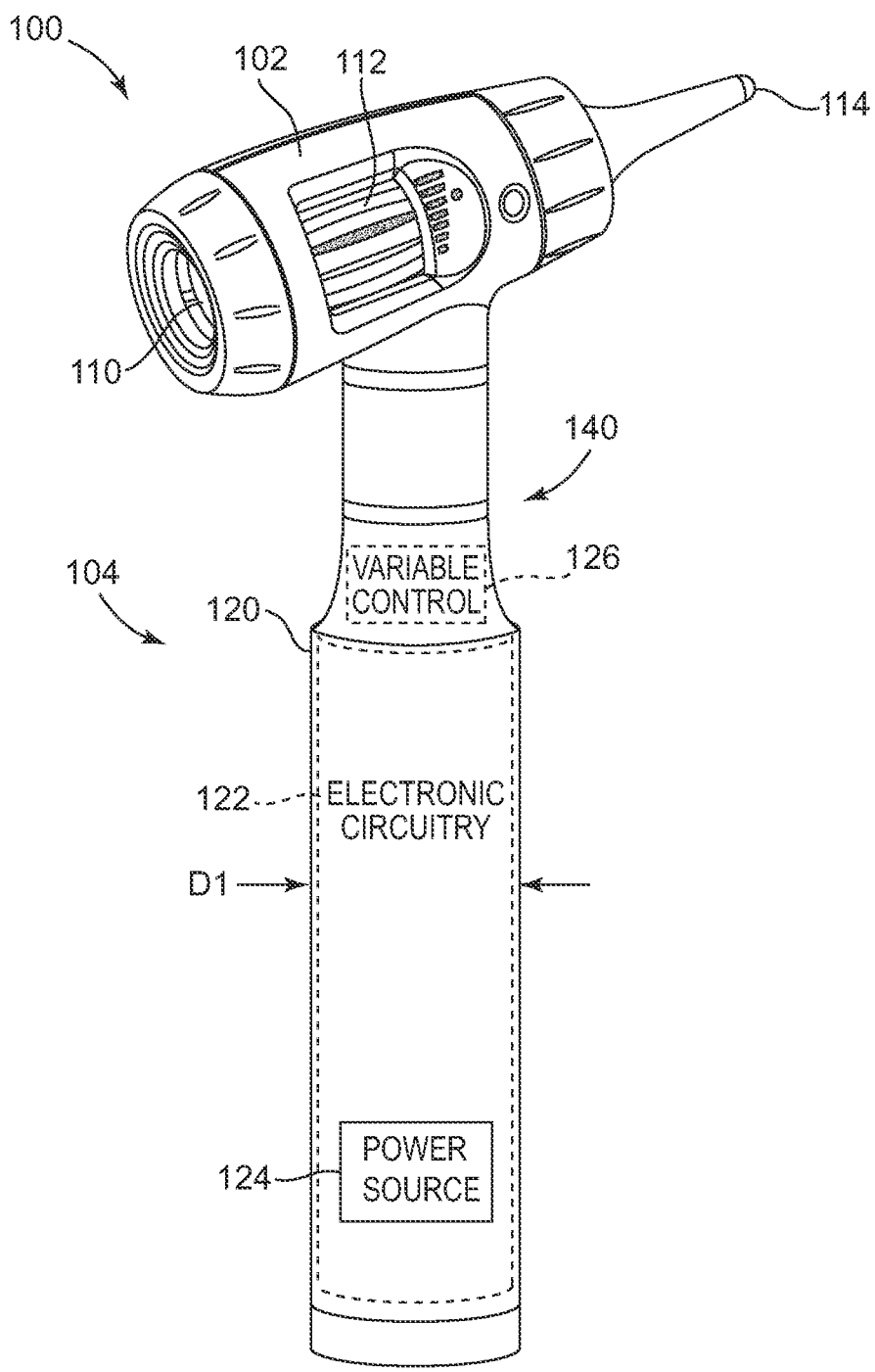
FIG. 1 is a schematic perspective view of an example handheld device.

Various embodiments will be described in detail with reference to the drawings, wherein like reference numerals represent like parts and assemblies throughout the several views. Reference to various embodiments does not limit the scope of the claims attached hereto. Additionally, any examples set forth in this specification are not intended to be limiting and merely set forth some of the many possible embodiments for the appended claims.

FIG. 1 is schematic perspective view of an example handheld device 100. In this example, the handheld device 100 includes an instrument 102 and a power handle 104.

An example of instrument 102 is an otoscope, which includes an adjustable optics assembly 110, an adjustment control 112, and a light source 114. An otoscope can be used by a healthcare provider during a patient encounter to view inside a patient's ear canal. To do so, the healthcare provider inserts the end of the otoscope into the ear canal, where it is illuminated by the light source 114. The healthcare provider then looks through the optics assembly 110 and adjusts the focus, if necessary, using the adjustment control 112. As discussed below, the light source is powered by the power handle 104. Power is transferred through conductors within the instrument.

A wide variety of instruments 102 can be used in other embodiments. In some embodiments, the instrument 102 is a medical examination instrument, such as an otoscope, an ophthalmoscope, a thermometer, a sphygmomanometer, a skin surface microscope, a unidirectional occluder, an examination light, an electronic stethoscope, a tympanometric instrument, an audiometer, or a variety of other medical examination instruments. In other embodiments, the instrument 102 is a therapeutic device, such as a surgical instrument, a drug delivery or measurement instrument, or other therapeutic devices. Although exemplary embodiments are described as handheld medical devices, other embodiments are possible, such as non-handheld devices, or non-medical devices.

The power handle 104 forms a handle for the handheld device 100, and is sized to be held in the hand of the healthcare provider. In this example, the power handle 104 includes a housing 120 and electronic circuitry 122 within the housing 120. The electronic circuitry 122 includes, for example, a power source 124, such as one or more batteries, capacitors, power cords, power input ports, or other power sources. In some embodiments, the power handle 104 further includes a variable control 126 within the housing 120 configured to receive input from a user, such as a healthcare provider.

The housing 120 is, in some embodiments, sized and configured to be held by a hand of a healthcare provider. The housing 120 is typically formed of materials such as metal or plastic, and forms a protective enclosure for the electronic circuitry 122 contained within the housing 120. A portion of the housing 120 that encloses the variable control 126 is typically an insulating material, such as a plastic, as discussed herein.

In some embodiments, the housing 120 has a cross-sectional dimension D1 sized to fit within a hand of a healthcare provider. In one example, the dimension D1 is in a range from about 0.5 inches to about 4 inches. In another example, the dimension D1 is in a range from about 0.5 inches to about 0.2 inches. In yet another example, the dimension D1 is about one inch. In some embodiments, at least a portion of the housing has a cylindrical shape, in which case the dimension D1 is the diameter of the housing.

In some embodiments, the housing 120 of the power handle 104 is sealed. As discussed herein, some embodiments include a variable control 126 that is enclosed within housing 120. This prevents liquid or particle intrusion into the housing at the variable control 126, improving the durability of the power handle 104. Similarly, some embodiments are powered with a rechargeable power source that does not need to be replaced during the life of the power handle 104. As a result, the power source can also be sealed within the housing 120 and does not require any doors or other openings, other than at the interface 140. A sealed housing 120 reduces the chance of water or other liquid or particle intrusion into the interior of housing 120. A sealed housing 120 is also easier to clean and sanitize.

In some embodiments, the electronic circuitry 122 includes the power source 124 as well as other control and power supply electronics, as described in more detail herein.

An example of a power source 124 is one or more batteries, such as alkaline or rechargeable batteries, that store electrical energy for powering the instrument 102, as well as the electronic circuitry 122. Another example of a power source 124 is a capacitive power source, including one or more capacitors for storing electrical energy. In some embodiments, however, the power source 124 is not contained within the housing 120. For example, a wall receptacle is used as a power source in some embodiments, which delivers power through a power cord extending from housing 120. Other power sources are used in other embodiments.

Some additional examples of a suitable power source 124 are described in co-pending U.S. patent application Ser. No. 13/102,108, by Robert J. Wood, filed on even date, and titled CAPACITIVE POWER SUPPLY FOR HANDHELD DEVICE, the disclosure of which is incorporated by reference herein in its entirety.

A variable control 126 is provided in some embodiments to permit adjustment of the operation of the power handle 104 or instrument 102. For example, in some embodiments the variable control 126 is used to adjust the amount of power delivered from the power handle 104 to the instrument 102. Examples of the variable control 126 are described in more detail herein, such as with reference to FIGS. 6-9.

In some embodiments the instrument 102 is connected to the power handle 104 at an interface 140. The interface 140 typically includes a mechanical interface, such as mating screw threads, or a snap together connection, and also an electrical interface to transfer power from the power handle 104 into the instrument 102. In some embodiments the instrument 102 can be disconnected from the power handle 104 at the interface. The interface 140 can be used in a variety of different types of instruments, to permit a single configuration of power handle 104 to be used with multiple different types of instruments. In other possible embodiments, however, instrument 102 is a single unit that includes the components of the power handle 104 within the housing of instrument 102, rather than within a separate power handle.

Figure 2:
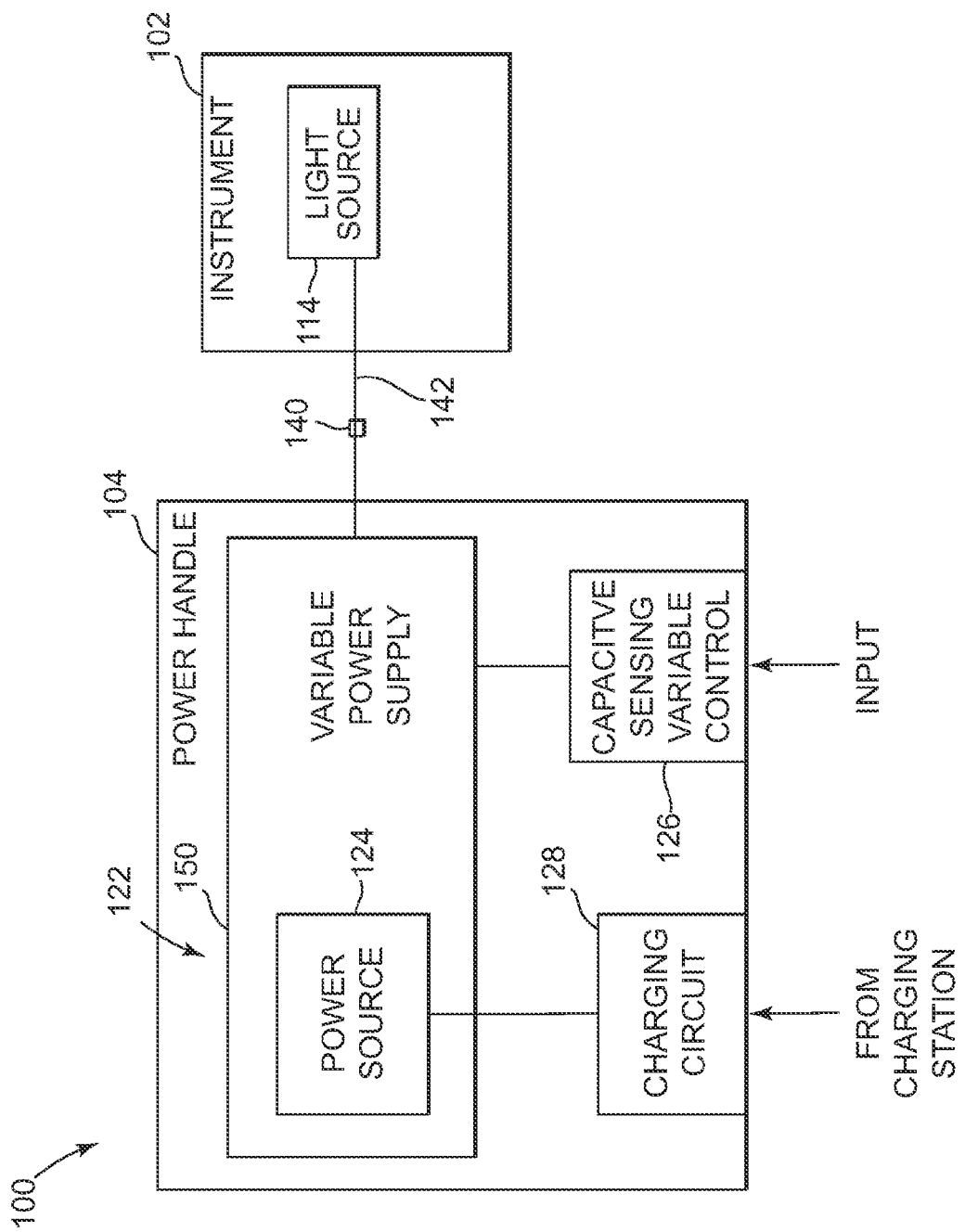
FIG. 2 is an electrical block diagram of the example handheld device, including an instrument and a power handle.

FIG. 2 is an electrical block diagram illustrating an example of the handheld device 100. As shown in FIG. 1, the example handheld device 100 includes an instrument 102 and a power handle 104. The instrument 102 includes an electronic device, such as a light source 114. The power handle 104 includes, for example, a variable power supply 150, a variable control 126, and a charging circuit 128. The variable power supply 150 includes a power source 124.

In some embodiments, the instrument 102 is an electronic instrument including one or more electronic devices requiring electrical power, such as a light source 114. Examples of the light source 114 include a halogen bulb and a light emitting diode. Other embodiments include other electronic devices or combinations of electronic devices within the instrument 102. The instrument 102 receives power from the power handle 104 through one or more conductors 144. The conductors 142 pass electrical power through the interface 140 between the power handle 104 and the instrument 102.

In some embodiments, the operation of the electronic device is variable. For example, the light source 114 is a dimmable bulb, which generates a variable intensity light output depending on the power received from the variable power supply. In some embodiments the light source 114 is adjustable between an off state and a full intensity state by adjusting a voltage supplied to the light source 114. In another embodiment, the light source 114 is adjustable by adjusting a duty cycle of a pulse-width modulated signal supplied to light source 114.

Variable power supply 150 generates an output that is delivered to instrument 102, such as through the interface 140. The output is used to power the light source 114, or other electronic devices in instrument 102. In some embodiments, the variable power supply provides a variable voltage output. In other embodiments, the variable power supply provides a variable power output, such as by pulse-width modulating the output signal.

The variable control 126 receives input from the user, which is passed to the variable power supply 150 and used by the variable power supply 150 to adjust the output. One example of the variable control 126 is shown in FIG. 3, and other examples are illustrated and described herein.

Some embodiments include charging circuit 128 that operates to charge the power source 124 when the power handle is placed into a charging station or plugged into a charging cord. The charging station or charging cord typically receives power from a wall receptacle. The charging circuit 128 converts the power into a form suitable for delivery to the power source 124.

Figure 3:
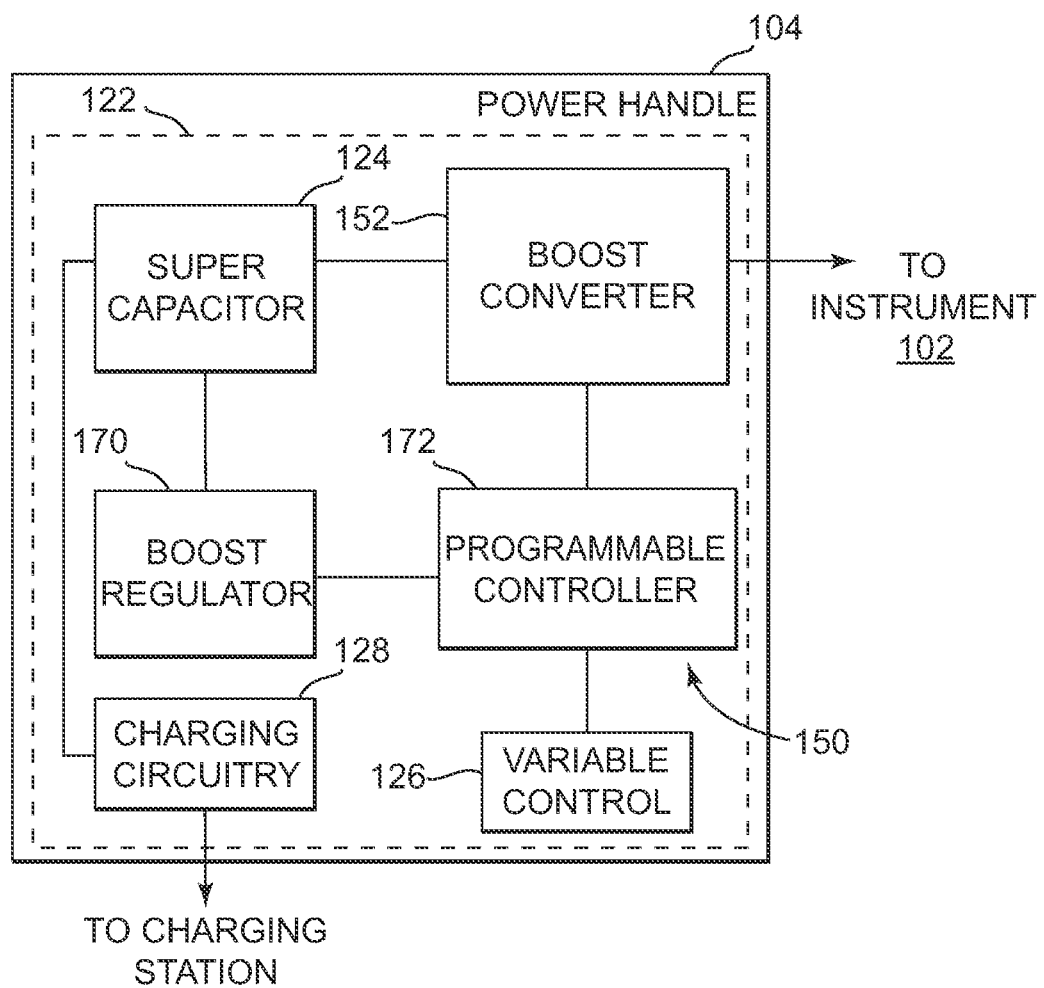
FIG. 3 is an electrical block diagram illustrating another example of the power handle shown in FIG. 2.

FIG. 3 is an electrical block diagram illustrating another example of the power handle 104. In this example, the power handle 104 includes electronic circuitry 122 including a capacitor as power source 124, a variable control 126, a variable power supply 150, and charging circuit 128. In this example, the variable power supply 150 includes a boost converter 152, a boost regulator 170, and a programmable controller 172. In this example, the power handle 104 provides a user variable power and/or a user variable output voltage to instrument 102 during operation, such as to permit the intensity of the light 114 (shown in FIG. 1) to be adjusted.

The variable power supply 150 receives power from power source 124, such as one or more super capacitors. A voltage at a capacitor decreases rapidly over time, and can quickly be reduced to below a minimum operating voltage required to power the instrument 102.

Accordingly, in this example the variable power supply 150 includes a boost converter 152 that boosts the voltage from the capacitor 124 to a desired level so that the electronic devices in the instrument 102 can continue to operate even after the voltage from the capacitor 124 has decreased below the minimum operating voltage.

In some embodiments, the boost converter 152 is an out bound buck-boost circuit that delivers a regulated output voltage until the voltage on the at least one capacitor has dropped to the minimum voltage that the specific electro-chemical construction allows. As one example, some embodiments continue to supply the regulated output voltage until the voltage on the at least one capacitor 124 has dropped to approximately 0.5v.

The variable control 126 receives input from the user, such as a healthcare provider, to turn the power handle 104 on and off. The variable control 126 also receives inputs from the user that indicate a desire for the power to the instrument 102 to be increased or decreased. The input from variable control is provided to the programmable controller 172.

The boost regulator 170 receives power from the capacitor 124 and modifies the power into a form required by the programmable controller 172, such as having a substantially constant fixed voltage. This power is then supplied to the programmable controller 172 to support the proper operation of the programmable controller 172.

The programmable controller 172 operates as an intelligent controller for the power handle 104. In some embodiments, data instructions are stored in a memory device, which may be a part of the programmable controller 172 (e.g., on-board memory) or a separate memory device that is readable by the programmable controller 12. The data instructions are executed by the programmable controller 172 to perform operations defined by the data instructions.

Figure 5:
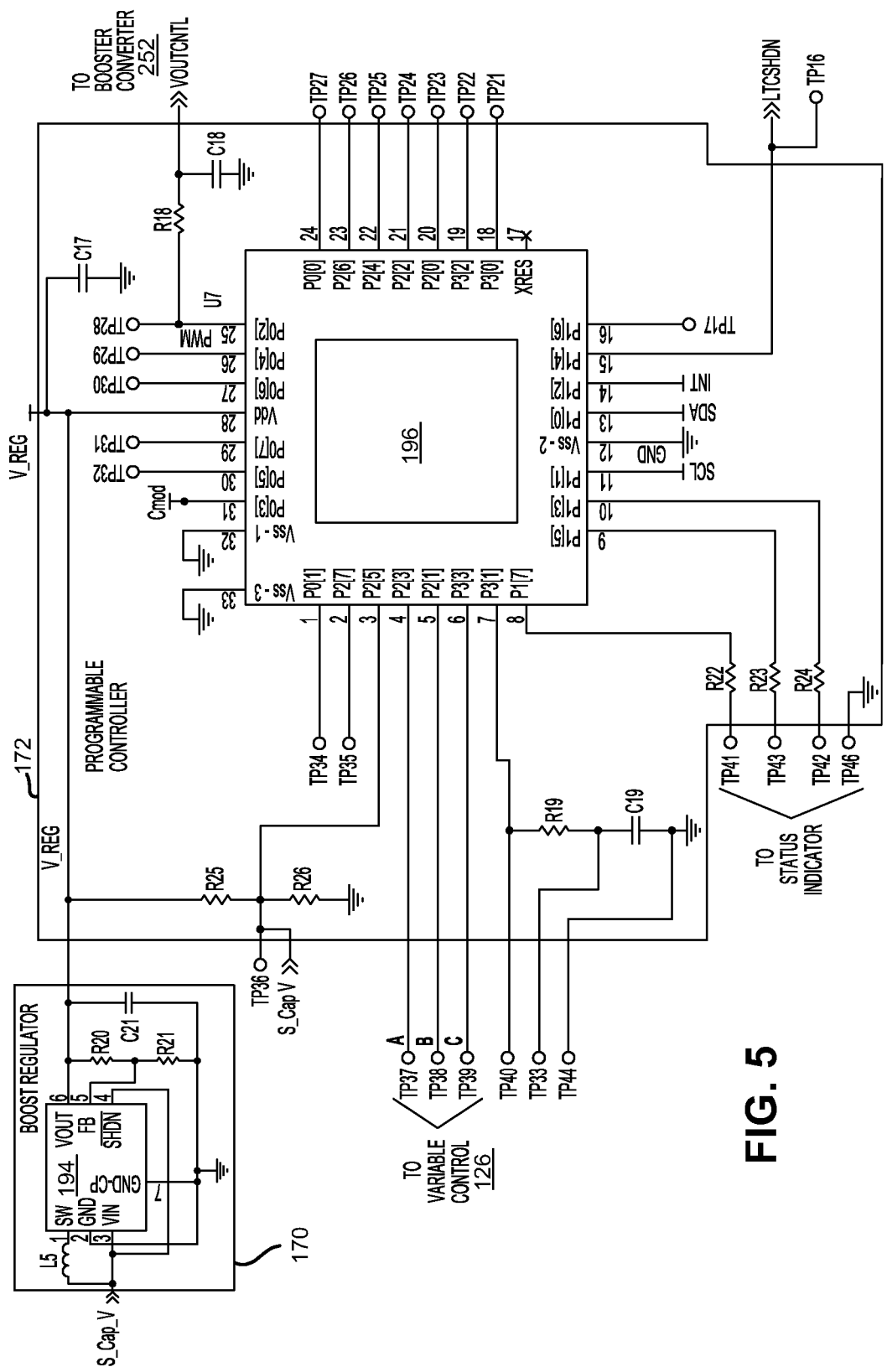
FIG. 5 is an electrical schematic of an example boost regulator and a programmable controller of the example power handle shown in FIG. 3.

One example of the programmable controller 172 is shown in FIG. 5, which includes a processing device. Examples of processing devices include microprocessors, central processing units, microcontrollers, programmable logic devices, field programmable gate arrays, digital signal processing devices, and the like. Processing devices may be of any general variety such as reduced instruction set computing devices, complex instruction set computing devices, or specially designed processing devices such as an application-specific integrated circuit device.

The programmable controller 172 receives user input from the variable control 126, and operates in conjunction with the boost converter 152 to generate a user variable output to the instrument 102. The boost converter 152 compensates for the decreasing voltage of the capacitor over time, while the programmable controller 172 provides inputs to the boost converter 152 to adjust the output power to the level desired by the healthcare provider.

Figure 4:
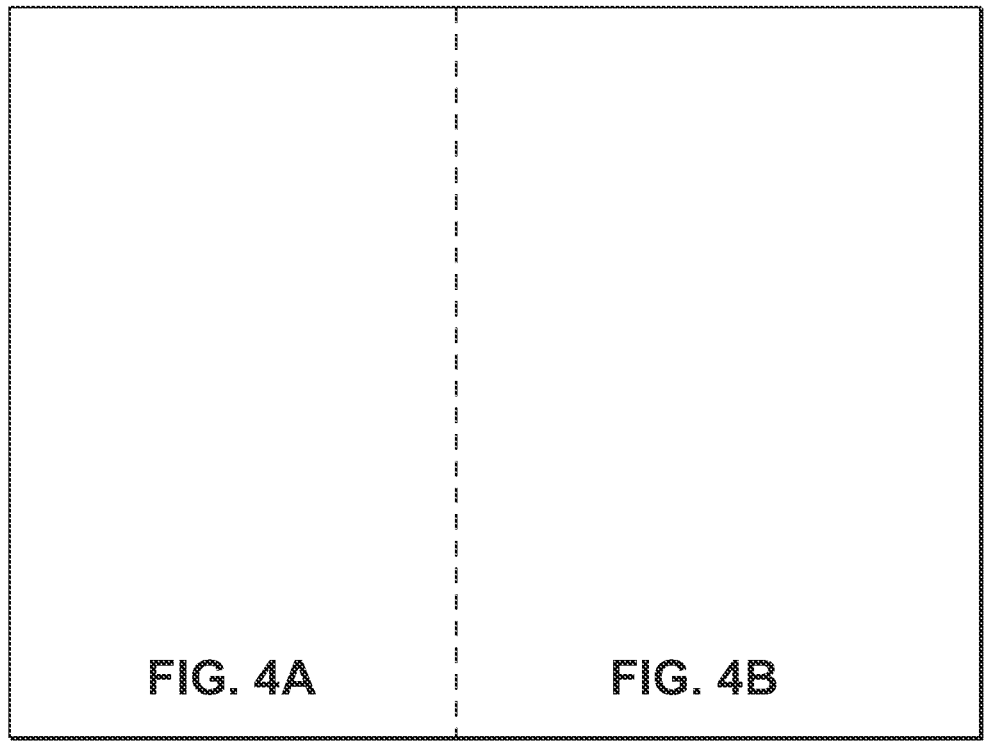
FIG. 4 illustrates an arrangement of FIGS. 4A and 4B.

FIGS. 4-5 illustrate a more detailed example of the power handle 104 shown in FIG. 3.

Figure 4A:
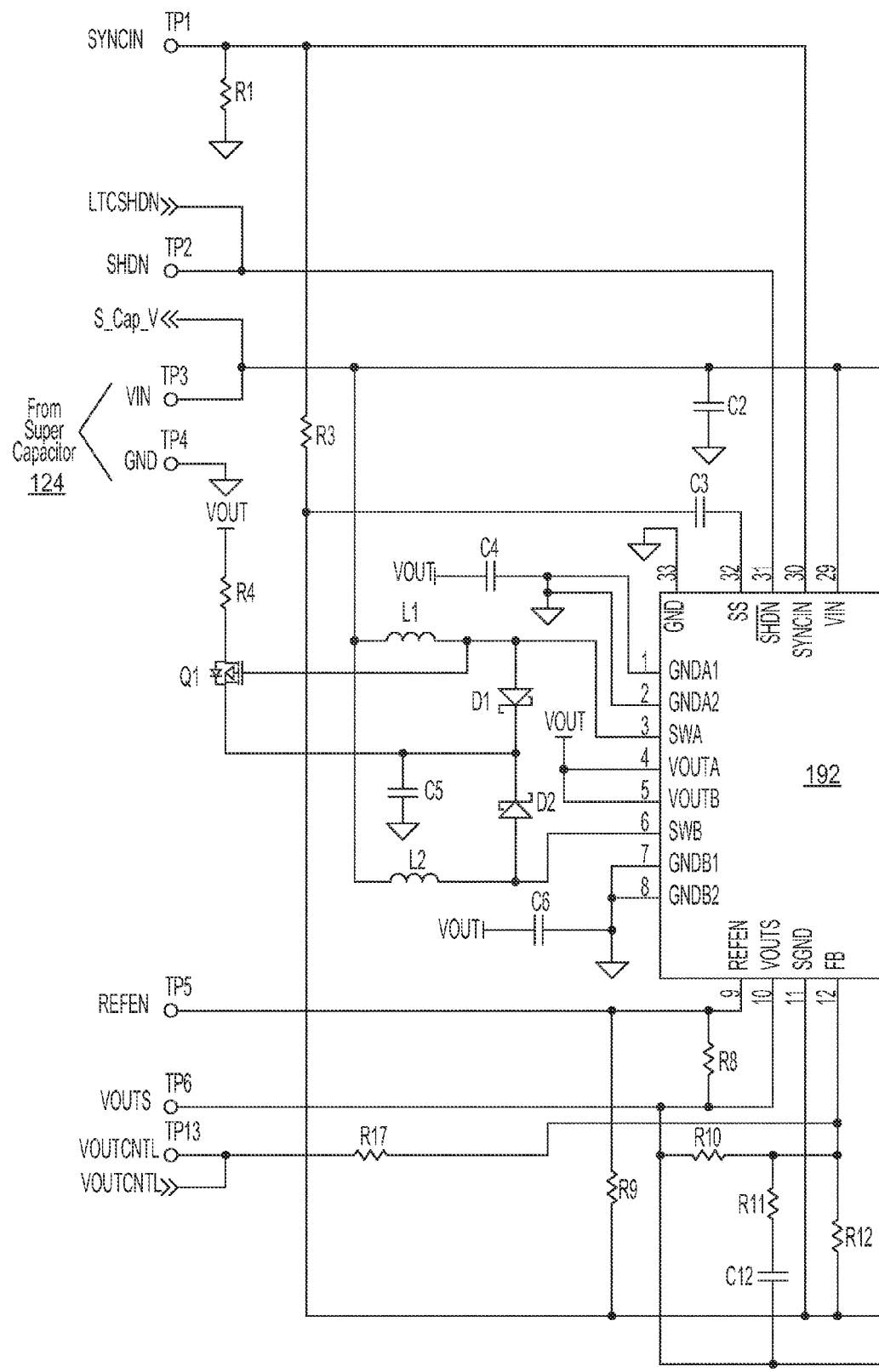
FIG. 4A is a first portion of an electrical schematic of an example boost converter of the example power handle shown in FIG. 3.
Figure 4B:
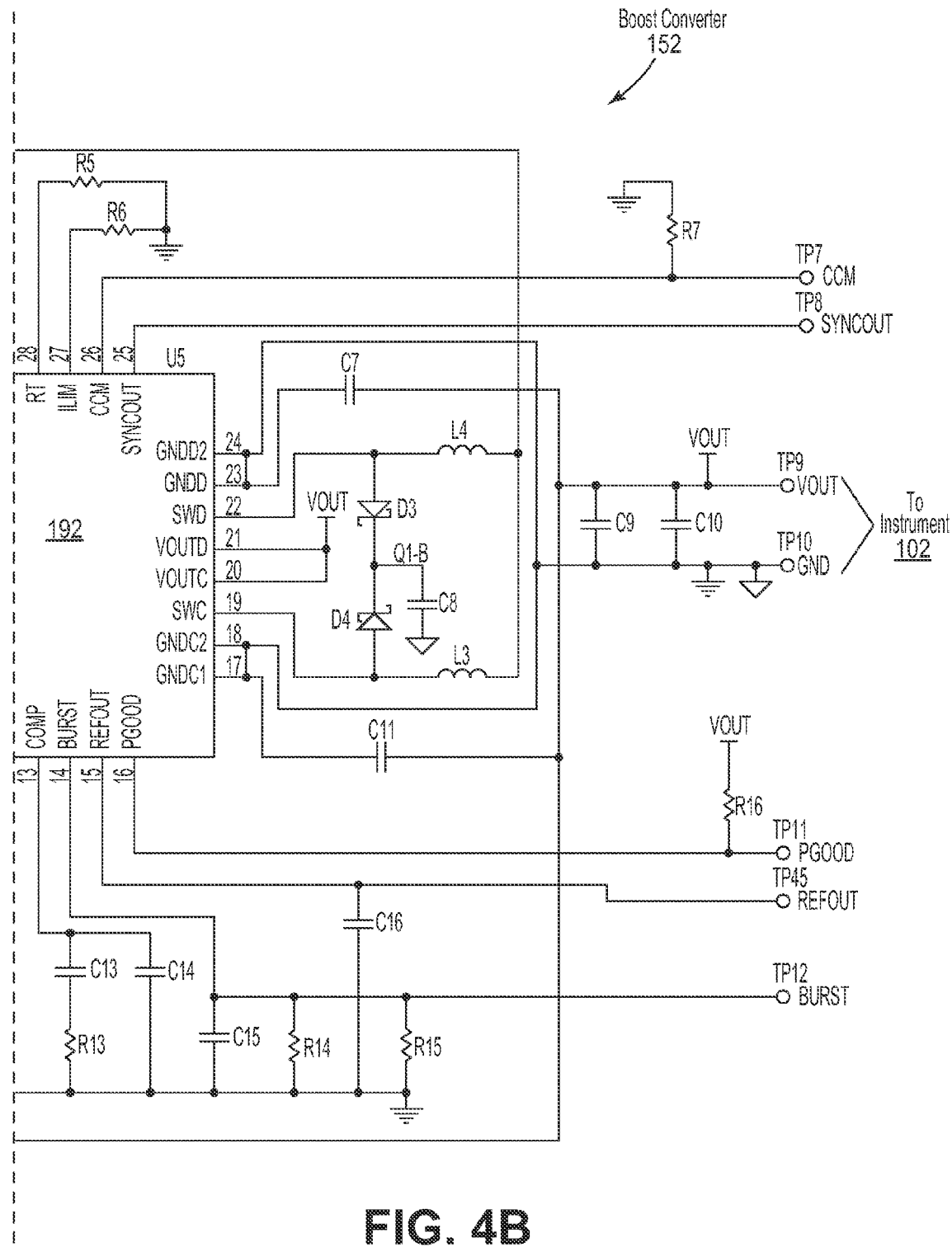
FIG. 4B is a second portion of the electrical schematic shown in FIG. 4A.

FIG. 4 (including FIGS. 4A and 4B) is an electrical schematic of an example boost converter 152 of the electronic circuitry 122 shown in FIG. 3. The boost converter 152 includes an integrated circuit 192, circuit points TP1 to TP12, inductors L1-L4, Schottky diodes D1 to D4, capacitors C1 to C16, resistors R1 to R15, and a metal oxide semiconductor field effect transistor (MOSFET) Q1.

The integrated circuit 192 is, for example, a 4-phase synchronous step-up DC/DC converter, such as Part No. LTC3425 distributed by Linear Technology Corporation of Milpitas, Calif. Other converters are used in other embodiments.

Power is received from the capacitor 124 at circuit point TP3, which is supplied to inductors L1, L2, L3, and L4, through Schottky diodes D1, D2, D3, and D4, and output by MOSFET Q1. The integrated circuit 192 detects the voltage being supplied by the capacitor and controls the switching of the circuit such that the voltage is increased across the inductors L1, L2, L3, and L4 to the desired level.

In this example, the boost converter 152 is also configured to receive an input from the programmable controller 172, shown in FIG. 5, to provide a user variable output voltage. The input is received by the boost converter 152 at the circuit point TP13 and is labeled as VOUTCNTL.

The output of the circuit at circuit point TP9, which is labeled as VOUT, is then provided to instrument 102.

FIG. 5 is an electrical schematic of an example circuit including a boost regulator 170 and a programmable controller 172. In this example, the boost regulator 170 includes an integrated circuit 194, an inductor L5, resistors R20 and R21, and a capacitor C21. The example programmable controller 172 includes a processing device 196, circuit points TP16 to TP46, resistors R18 to R26, and capacitors C17 and C18.

The integrated circuit 194 is, for example, a synchronous step-up dc/dc converter, such as Part No. LTC3526LB distributed by Linear Technology Corporation. The boost regulator 170 is coupled to the capacitor 124 at the circuit point labeled as S_CAP_V, and operates to generate a substantially constant fixed voltage output (labeled as VREG) as needed to operate the programmable controller 172.

The programmable controller 172 includes a processing device 196. An example of the processing device 196 is a programmable system-on-chip, such as Part No. CY8C21434 distributed by Cypress Semiconductor Corporation of San Jose, Calif. The programmable system-on-chip includes a CPU and memory devices. The memory devices include static random access memory (SRAM), static read only memory (SROM), flash memory. The programmable controller 172 can also include a variety of other devices, such as clocks, input/output interfaces, digital and analog electronics, etc.

The programmable controller 172 receives inputs from the variable control 126 at circuit points TP37, TP38, and TP39, and generates an appropriate output signal that is provided to the boost converter 152, at the circuit point labeled as VOUTCNTL. Circuit points TP37, TP38, and TP39 are inputs to the capacitance sensors provided by the programmable system-on-chip, where the inputs are received from the variable control 126. In one example, the circuit point TP37 is an input to a capacitance sensor A, the circuit point TP38 is an input to a capacitance sensor B, and the circuit point TP39 is an input to a capacitance sensor C.

In this example, the power handle 104 includes a status indicator, such as a light emitting diode (LED) indicator. The status indicator is operable to illuminate with a specific color indicative of a status of the power handle. In one example, the status indicator is a single indicator having three integral LEDs, including a red LED, a green LED, and a blue LED. The LEDs are operated by the programmable controller 172 to indicate the status. For example, a yellow status light indicates that the power handle 104 is in need of charging, a blue status light indicates that the power handle is charging, and a green status light indicates that the power handle 104 is fully charged.

Figure 6:
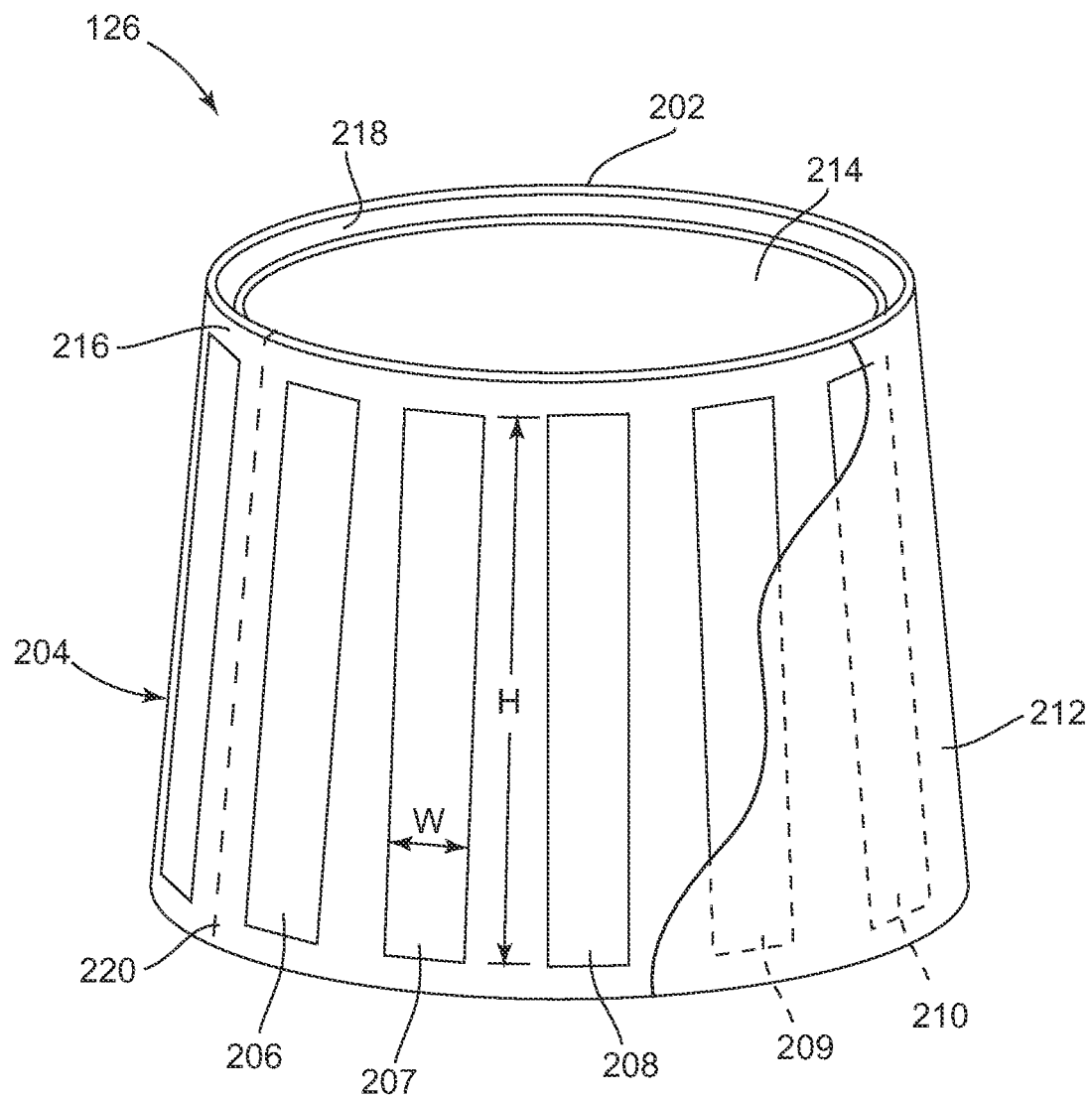
FIG. 6 is a perspective view of an example variable control of the handheld device shown in FIG. 1.

FIG. 6 is a perspective view of an example variable control 126. In this example, variable control 126 includes a flexible circuit board 202, electrical conductors 204, an insulating layer 212, and a conductive layer 214. The flexible circuit board 202 includes an outer surface 216 and an inner surface 218.

In some embodiments the circuit board 202 is formed of a flexible material. The material is typically manufactured in a flat shape, but can be bent into a desired shape, such as shown in FIG. 6. Ends of the circuit board 202 can be fastened together to form a joint 220, with any suitable fastener, such as a clip, adhesive, solder or weld joints, or other fasteners. Some embodiments are bent and joined together at joint 220 to form a circuit board 202 having a substantially circular cross section. The circuit board 202 is typically made from a substrate, such as a flexible plastic. The flexible circuit board 202 includes an insulating material, and can further include conductive traces formed on or within the insulating material. Additional electronic components can be formed on or fastened to the flexible circuit board 202. In some embodiments the circuit board 202 is rigid and substantially inflexible. In some embodiments the circuit board 202 is molded into the desired shape.

In this example, electrical conductors 204 are formed on outer surface 216 of the flexible circuit board 202. An example of a conductive material suitable for electrical conductors 204 is copper. Gold or other suitable metals or conductive materials are used in other embodiments. The electrical conductors include conductors 205, 206, 207, 208, 209, 210, and other electrical conductors. Some embodiments include a quantity of electrical conductors 204 in a range from about 3 to about 50, and preferably from about 9 to about 18. One example includes 12 conductors 204.

The electrical conductors 204 are in the form of elongated strips, having a thickness, a width, and a height. Different embodiments can have different dimensions. As one example, the width W of the electrical conductors 204 is in a range from about 0.01 inches to about 0.25 inches. In another example, the width W is in a range from about 0.1 inches to about 0.15 inches. The height H of the electrical conductors 204 is in a range from about 0.5 inches to about 2 inches. In another example, the height H is in a range from about 0.7 inches to about 1.3 inches. Other embodiments have other dimensions. An example of the thickness of the conductor 204 is in a range from about 0.001 inches to about 0.05 inches. Other embodiments have other dimensions.

An insulating layer 212 is formed over electrical conductors 204 and the outer surface 216 of circuit board 202. In some embodiments the insulating layer 212 is a coating. In other embodiments, insulating layer 212 is a separate layer of material that is placed adjacent to outer surface 216 of circuit board 202. The insulating layer 212 forms at least a portion of housing 120 that protects and encloses the variable control 126.

Some embodiments include a conductive layer 214 formed on the inner side 218 of circuit board 202. The conductive layer 214 is separated from electrical conductors 204 by the insulating circuit board 202. In this way, the conductors 204 and the spaced conductive layer 214 form a plurality of capacitors distributed around the circuit board 202. In some embodiments the conductive layer 214 is a ground plane.

Figure 7:
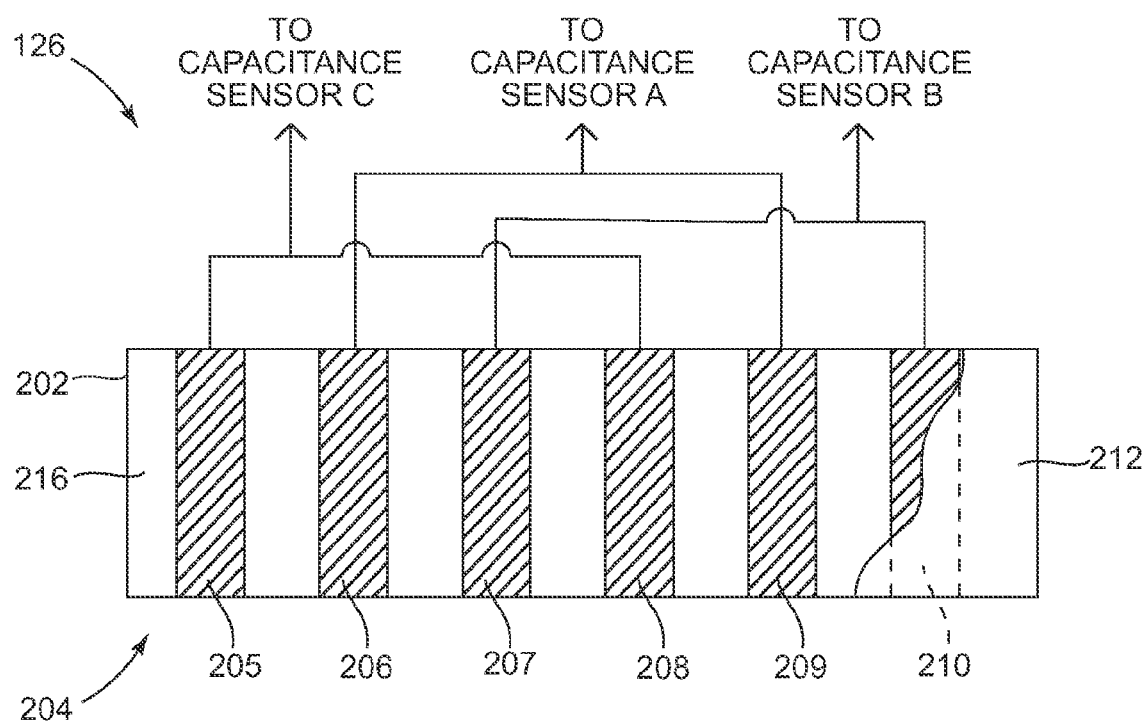
FIG. 7 is a plan view of another example variable control.

FIG. 7 is a plan view of another example variable control 126. In this example, the variable control 126 is formed of a substantially flat circuit board 202. In some embodiments the circuit board 202 is flexible and can be bent to have a substantially circular cross-sectional shape, or into another shape, as desired. In another embodiment, the circuit board 202 is substantially rigid, and maintains a substantially flat shape. For example, a straight circuit board can be included within a flat region of a device's housing, such as the top, side, or back of a mobile phone.

The variable control 126 shown in FIG. 7 includes features similar to that shown in FIG. 6, such as the electrical conductors 204 provided on the outer surface 216 of circuit board 202, an insulating layer 212 adjacent the electrical conductors 204, and in some embodiments a conductive layer (not visible in FIG. 7) along the rear surface of circuit board 202. Additional electronic components and electrical traces are included in some embodiments.

FIG. 7 also illustrates electrical connections between electrical conductors 204 and capacitance sensors. Although some embodiments include a separate capacitance sensor for each electrical conductor 204, the number of capacitance sensors can be reduced by connecting multiple electrical conductors 204 into a single capacitance sensor. In this example, three capacitance sensors are used, labeled as A, B, and C. More specifically, in this example capacitance sensor A is connected to conductors 206 and 209, capacitance sensor B is connected to conductors 207 and 210, and capacitance sensor C is connected to conductors 205 and 208. Additional conductors are included in some embodiments, and the additional conductors can be similarly connected to the capacitance sensors A, B, and C in an alternating fashion as shown in FIG. 7. By using at least three capacitance sensors, the direction of movement can be detected, as discussed with reference to FIG. 8.

Figure 8:
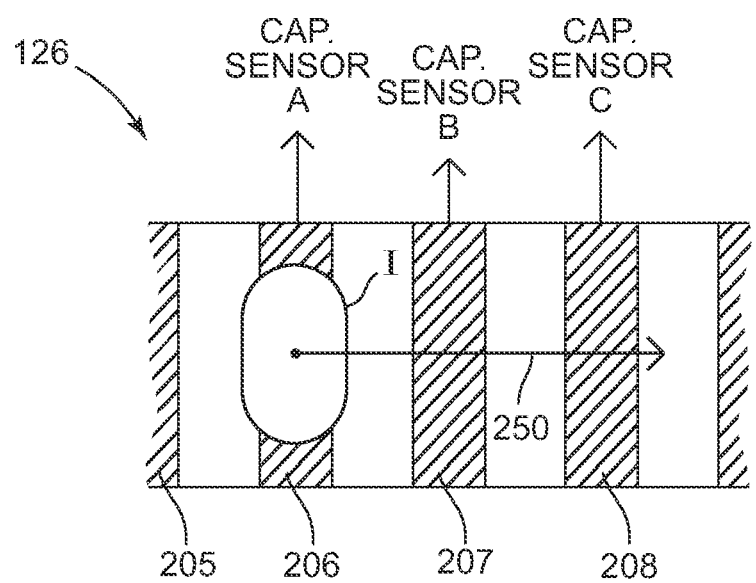
FIG. 8 is a plan view of the example variable control shown in FIG. 7, which illustrates the receipt of an input from a user.

FIG. 8 is a schematic block diagram of an example variable control 126 illustrating the receipt of an input from a user. An insulating layer 212 of the housing 120 is not shown in FIG. 8 in order for the electrical conductors 204 to be visible.

A user provides an input I to the variable control 126 by placing a finger on the housing in the vicinity of the variable control 126, such as adjacent to the conductor 206. Upon doing so, the capacitance sensor A detects a change in the capacitance at the conductor 206. For example, an increased capacitance is detected.

The user then moves the finger across the variable control 126 in the direction of arrow 250. As the input I from the finger moves away from conductor 206, the capacitance sensor A detects a decrease in the capacitance, while the capacitance sensor B detects an increase in capacitance at conductor 207. If the input continues in the direction of arrow 250, the capacitance sensor B detects a decrease in the capacitance as the input I from the finger moves beyond conductor 207 and toward conductor 208, at which time the capacitive sensor C detects an increase in capacitance.

Figure 9A:
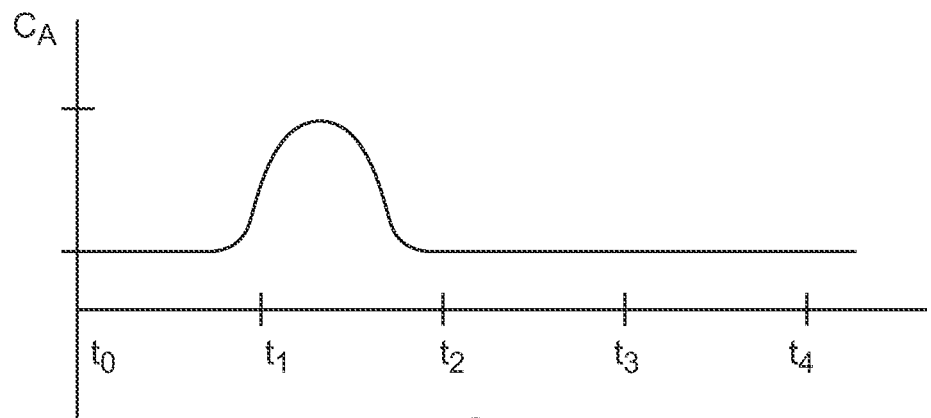
FIG. 9 is a schematic diagram illustrating the detected capacitances at several capacitance sensors upon receipt of the input shown in FIG. 8.
Figure 9B:
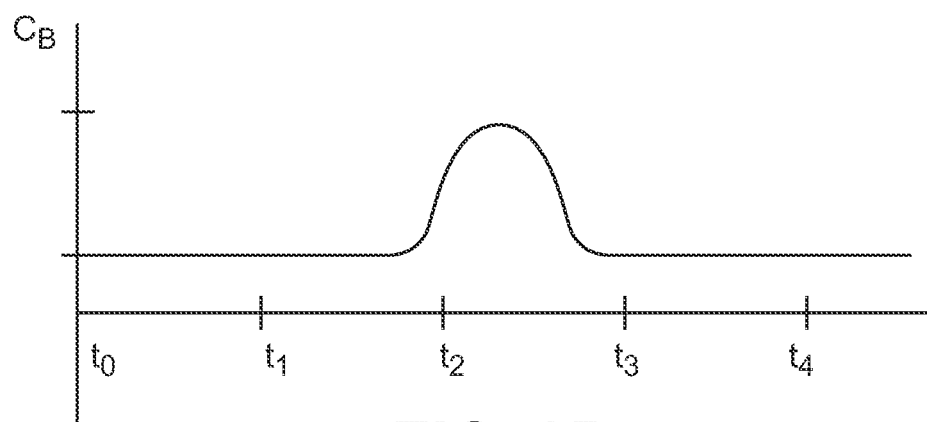
Figure 9C:
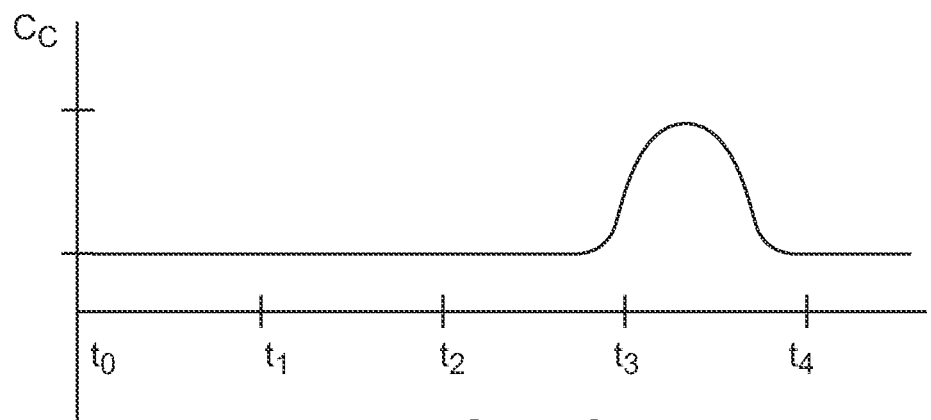

FIG. 9 is a schematic diagram illustrating the detected capacitances at each capacitance sensor upon receiving an input I as shown in FIG. 8. Three graphs are illustrated in FIG. 9, which show the capacitance detected by three difference capacitance sensors over the same period of time. The first graph shows the capacitance detected by a capacitance sensor A ($C_A$), the second graph shows the capacitance detected by a capacitance sensor B ($C_B$), and the third graph shows the capacitance detected by a capacitance sensor C ($C_C$).

At time $t_0$, no input is being provided to the variable control 126, and so capacitance sensors CA, CB, and CC all detect approximately the same nominal capacitance, which is, for example, the sum of the capacitances between each conductor 204 connected to the respective capacitance sensor, and the conductive layer 214 along a rear surface of the circuit board 202 (e.g., shown in FIG. 6).

At time $t_1$, the input I is provided to the variable control 126, in which the user places a finger on the variable control 126 adjacent to conductor 206, as shown in FIG. 8. The presence of the finger causes capacitance sensor A to detect an increase in the capacitance at time $t_1$.

The user then moves the finger in the direction of arrow 250, shown in FIG. 8. The input I is detected by capacitance sensor A as a decrease in capacitance, but as an increase in capacitance by capacitance sensor B. As a result, at time $t_2$ the capacitance has returned to the nominal level at capacitance sensor A, but has increased at capacitance sensor B. As a result, the movement can be determined by the processor to be in the direction of arrow 250.

If the movement continues in the direction of arrow 250, the capacitance sensor B detects a decrease in capacitance, while the capacitance sensor C detects an increase in capacitance. When the finger is adjacent conductor 208 at time $t_3$, the capacitance detected by capacitance sensor B has returned to the nominal level, while the capacitance at capacitance sensor C has increased. The movement is determined by the processor to have continued in the direction of arrow 250, by determining the order in which the capacitance sensors detect an increase in capacitance. For example, A, B, and then C. Similarly, any input that proceeds in the order of A to B, B to C, or C to A, will correctly be identified as being in the direction of arrow 250.

The finger is then removed from the variable control 126, causing all capacitance sensors to detect a nominal capacitance at time $t_4$.

The variable control can similarly receive an input I in the opposite direction as arrow 250. For example, an input can be provided by placing a finger adjacent conductor 208, and then moved across conductors 207, and then conductor 206. In this case, the capacitance will be detected in the order of C, B, and then A. Similarly, any input that proceeds in the order of C to B, B to A, or A to C will be correctly identified as being in the opposite direction as arrow 250.

The input I detected by the capacitance sensors is then utilized to adjust the operation of the device 100. For example, the input is used in some embodiments to adjust the power or voltage output from variable power supply 150.

The speed of the input I is also detected in some embodiments. The speed of movement can be determined by the amount of time between transitions, for example, the difference between time $t_1$ and time $t_2$. In some embodiments, a faster movement causes the variable power supply 150 to make a larger magnitude adjustment in to the output, and a slower movement causes the variable power supply 150 to make a smaller magnitude adjustment in the output.

In some embodiments, the direction of a first input I that is received from a user sets an increase direction for that use. For example, if a first input I is in the direction of arrow 250, shown in FIG. 8, the direction of arrow 250 is set as an increase direction. If further input is received in the direction of arrow 250, the output is further increased. If further input is received in the direction opposite arrow 250 (e.g., a decrease direction), the output is decreased.

On the other hand, if the first input I is in the direction opposite arrow 250, that direction is set as the increase direction. Further input received in the direction opposite arrow 250 causes the output to be increased. If further input is received in the direction of arrow 250 (e.g., the decrease direction), the output is decreased. In some embodiments the input direction is reset when the device is turned off (e.g., by providing one or more inputs in the decrease direction, by returning the device to a charging station, or by selecting an off button).

The various embodiments described above are provided by way of illustration only and should not be construed to limit the claims attached hereto. Those skilled in the art will readily recognize various modifications and changes that may be made without following the example embodiments and applications illustrated and described herein, and without departing from the true spirit and scope of the following claims.

What is claimed is:

1. A device comprising:
    a handheld medical instrument including an electronic device, wherein the handheld medical instrument is selected from: an otoscope, an ophthalmoscope, a thermometer, a sphygmomanometer, a skin surface microscope, a unidirectional occluder, an examination light, an electronic stethoscope, a tympanometric instrument, and an audiometer; and
    a power handle coupled to the electronic device, the power handle comprising:
    a variable control that detects a capacitance of and movement of a user's finger on an external surface of the power handle, the variable control comprising at least three spaced conductive strips separated from the exterior surface by an electrically insulating material, wherein the variable control generates a control signal upon detection of changes in capacitance at the spaced conductive strips in response to the movement of the user's finger across the external surface of the power handle; and
    a variable output power supply electrically connected to the electronic device and configured to receive the control signal from the variable control, wherein the variable output power supply supplies a variable voltage output to the electronic device based on the control signal.

2. The device of claim 1, wherein the at least three spaced conductive strips are each separately connected to a capacitance sensing circuit that detects capacitance changes.

3. The device of claim 1, wherein the at least three spaced conductive strips comprise at least six spaced conductive strips, wherein a first and a fourth conductive strip are electrically connected to a first capacitance sensing circuit, a second and a fifth conductive strip are electrically connected to a second capacitance sensing circuit, and a third and a sixth conductive strip are electrically connected to a third capacitance sensing circuit.

4. The device of claim 1, wherein the capacitance sensing variable control comprises a flexible circuit board wherein the at least three spaced conductive strips are formed on a first surface of the flexible circuit board.

5. The device of claim 4, wherein the flexible circuit board includes a conductive layer formed on a second surface, the second surface opposing the first surface.

6. The device of claim 4, wherein the flexible circuit board is bent to have a substantially circular cross sectional shape, and wherein ends of the flexible circuit board are joined together.

7. The device of claim 1, wherein the variable output power supply comprises a boost converter and a programmable controller, the programmable controller electrically coupled to the variable control and programmed to detect an input at the variable control, and the boost converter electrically coupled to the programmable controller to receive an signal from the programmable controller to adjust the output of the variable output power supply based on the input.

8. The device of claim 7, wherein the instrument is an otoscope and wherein the electronic device is a variable intensity light generator.

9. The device of claim 1, wherein the medical instrument is an otoscope and wherein the electronic device is a variable intensity light generator.

10. A device comprising:
an otoscope including a variable intensity light generator, wherein the intensity of light generated by the light generator is modified by changing a magnitude of power supplied to the light generator; and
a power handle coupled to the otoscope, the power handle comprising:
    a housing including an external surface;
    a capacitance sensing variable control sealed within the housing and separated from the external surface by an insulating material, the capacitance sensing variable control including at least three spaced conductive strips arranged and configured to detect changes in capacitance at the conductive strips indicative of a sliding movement of a finger along the external surface, wherein the capacitive sensing variable control generates a control signal when a user's finger moves across the external surface by detecting changes in capacitance at the spaced conductive strips;
    a power source within the housing; and
    a variable power supply within the housing and electrically coupled between the power source and the light generator, wherein the variable power supply receives the control signal from the capacitance sensing variable control and adjusts the power supplied to the light generator based on the control signal.

11. The device of claim 10, wherein the spaced constructive strips are spaced about a perimeter of the housing, and wherein every third conductive strip is electrically connected to a common capacitance sensor.

12. The device of claim 10, further comprising a flexible circuit board having the conductive strips arranged on the flexible circuit board, and an insulating material arranged adjacent the conductive strips and forming at least a portion of the housing and the external surface.

13. The device of claim 10, wherein the power source is at least one capacitor providing the primary energy storage for the device.

14. The device of claim 10, wherein the otoscope and the power handle are separable at an interface.

* * * * *